United States Patent
Heimberger et al.

[11] Patent Number: 5,562,699
[45] Date of Patent: Oct. 8, 1996

[54] FORCEPS

[75] Inventors: Rudolf Heimberger, Oberderdingen; Uwe Schaumann, Knittlingen, both of Germany

[73] Assignee: Richard Wolf GmbH, Knittlingen, Germany

[21] Appl. No.: 413,375

[22] Filed: Mar. 30, 1995

[30] Foreign Application Priority Data

Mar. 30, 1994 [DE] Germany ................ 44 11 099.5

[51] Int. Cl.[6] ................................................ A61B 17/28
[52] U.S. Cl. ...................... 606/205; 606/206; 606/208; 606/170; 128/751
[58] Field of Search .................... 128/751; 606/205, 606/206, 207, 208, 170

[56] References Cited

U.S. PATENT DOCUMENTS

| | | | |
|---|---|---|---|
| 1,127,948 | 2/1915 | Wappler | 606/170 |
| 5,009,661 | 4/1991 | Michelson | 606/205 |
| 5,044,947 | 9/1991 | Sachdeva et al. | |
| 5,242,458 | 9/1993 | Bendel et al. | |
| 5,254,130 | 10/1993 | Poncet et al. | 606/205 |

FOREIGN PATENT DOCUMENTS

| | | | |
|---|---|---|---|
| 450608A1 | 10/1991 | European Pat. Off. | 606/205 |
| 4313903 | 9/1994 | Germany . | |
| 9205828 | 4/1992 | WIPO . | |
| 9325267 | 12/1993 | WIPO . | |

*Primary Examiner*—Michael Powell Buiz
*Assistant Examiner*—Mark S. Leonardo
*Attorney, Agent, or Firm*—Cohen, Pontani, Lieberman, Pavane

[57] ABSTRACT

A surgical instrument such as a forceps having a handle at its proximal end, a pair of jaws at its distal end for gripping an object, and a connecting member for transmitting user-applied force from the handle to the pair of jaws. The connecting member includes a force transmitting and limiting member for transmitting the closure force imparted by the jaws upon the object to a predetermined value. The force transmitting and limiting member is preferably made of a material that is superelastic (i.e. reversibly deformable such that it returns to its original physical shape or form after the material has been deformed substantially) and is comprised of a rod, a spring or a portion of a scissors-shaped forceps. The extent of relative movement of the handle grips is limited by a stop to prevent the superelastic material from undergoing excessive deformation.

11 Claims, 5 Drawing Sheets

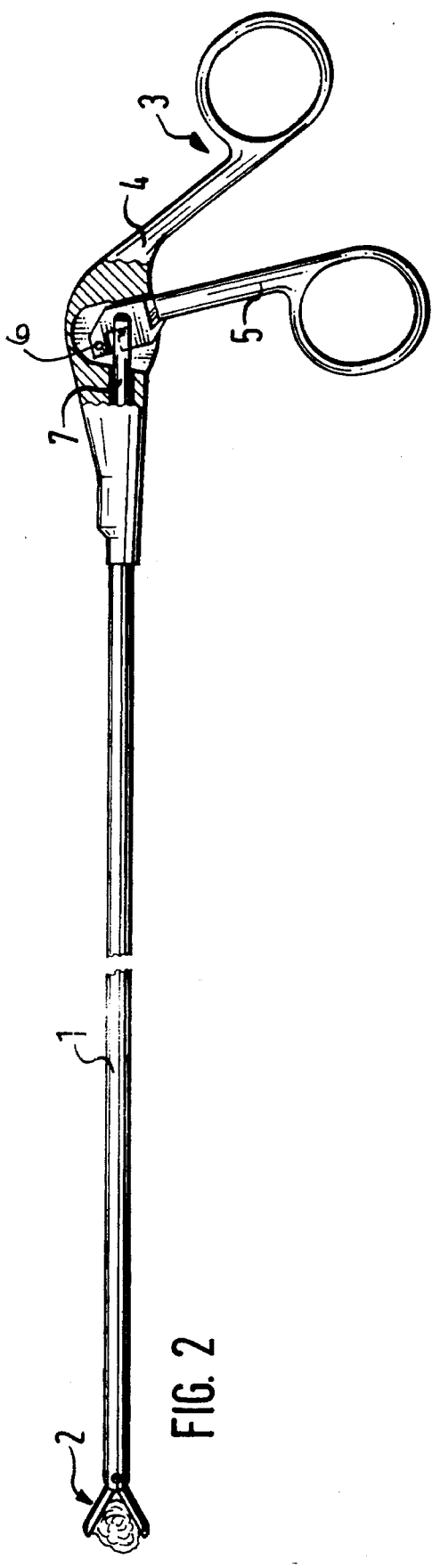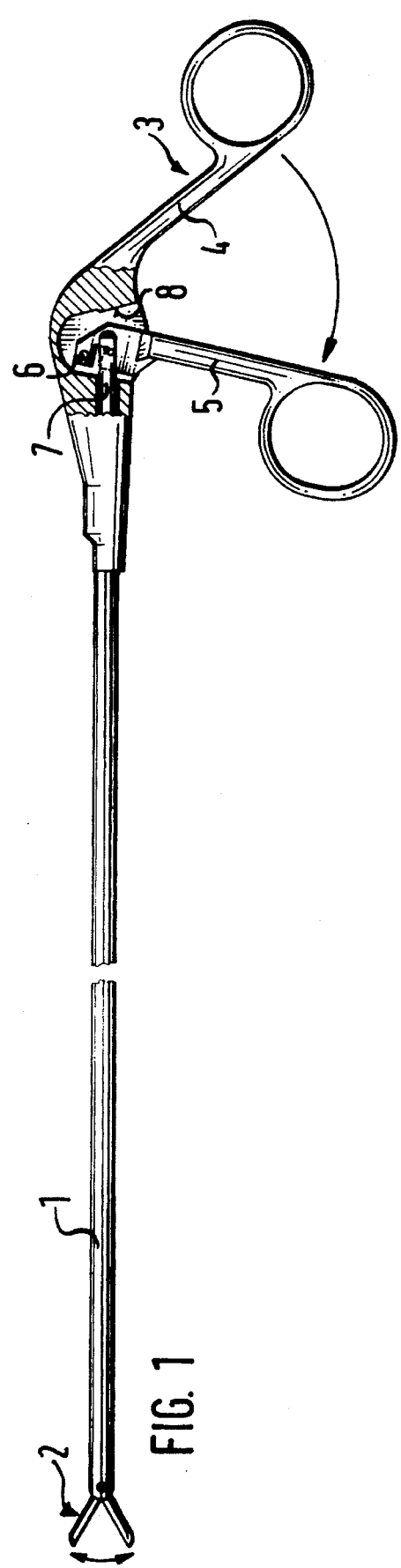

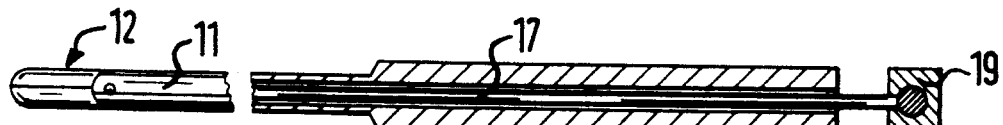
FIG. 3
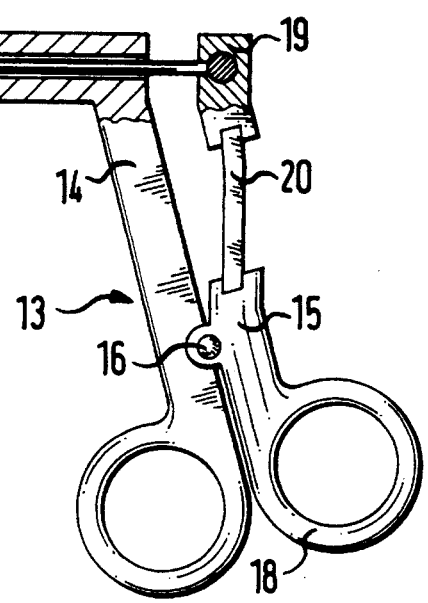
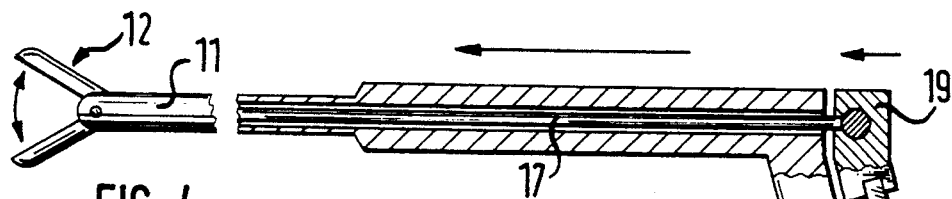
FIG. 4
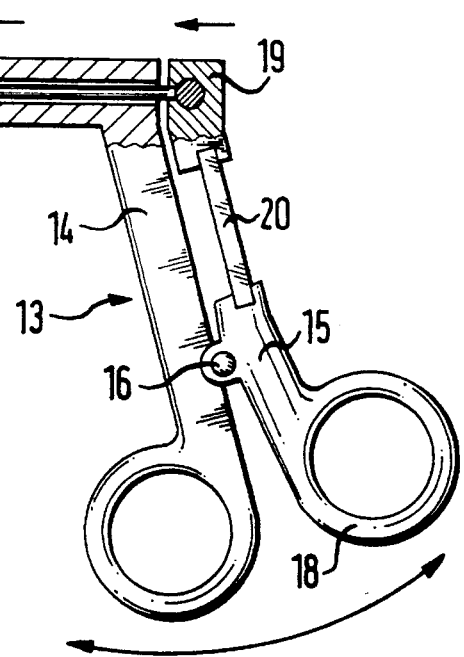

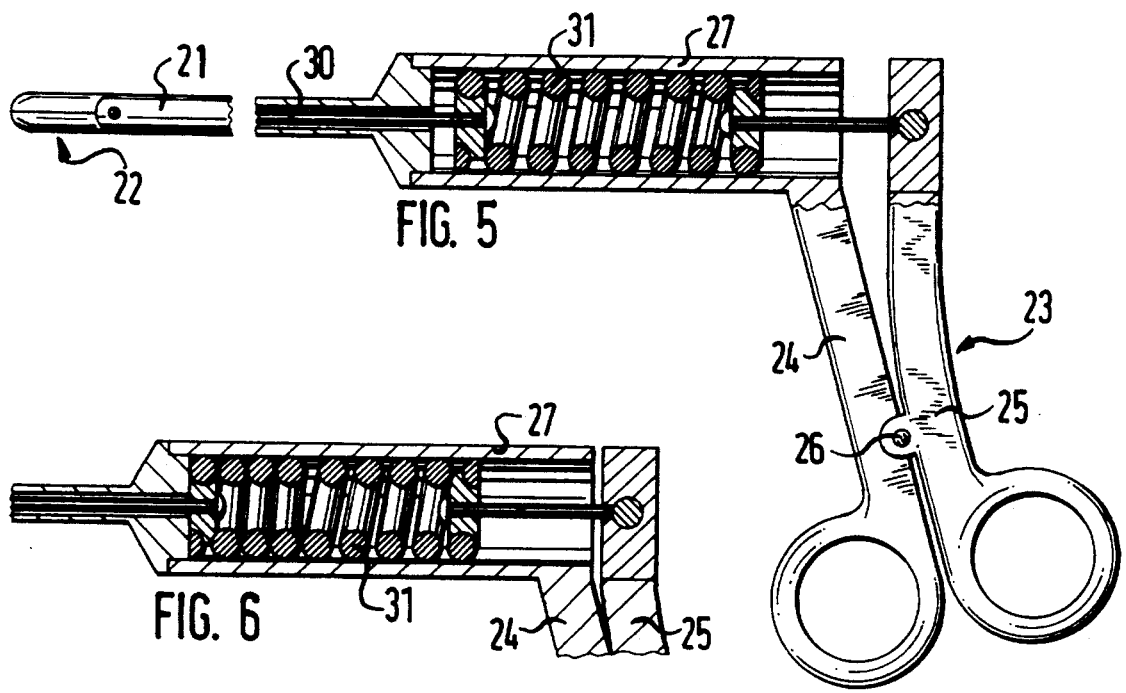
FIG. 5
FIG. 6
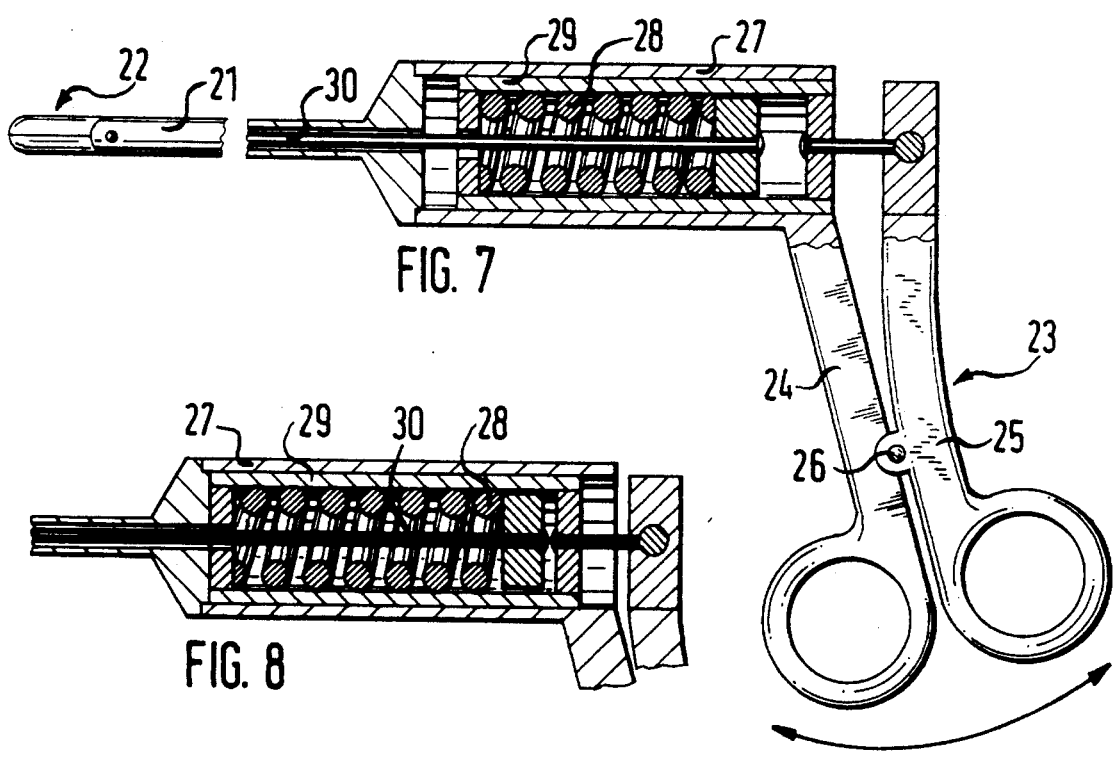
FIG. 7
FIG. 8

FORCEPS

BACKGROUND OF THE INVENTION

1. Field of the Invention

The present invention relates to a medical instrument such, for example, as a forceps, a scissor-type instrument or needle holder, with a pair of distal jaws, a proximal handle which actuates gripping motion to the jaws, and a means for limiting the holding force of the jaws to a predetermined maximum value.

2. Description of the Prior Art

German Patent document DE-A 36 01 166 discloses a forceps for gripping tissue of a patient. The forceps has a fixed jaw and a movable jaw, the fixed jaw being connected to a fixed grip and the movable jaw being connected to a pivotable grip. To limit the compressive force that the jaws can exert on the tissue, the pivotable grip is divided into two pieces —an upper and a lower piece. The two pieces are articulated or joined to one another and supported against each other by a spring member. In operation, when the applied pressure exceeds a predetermined value, the lower piece becomes deflected relative to the upper piece so that the pivotable grip can no longer pivot. However, upon further movement of the pieces towards each other, the holding force of the jaws increases, depending on the stiffness of the spring member. Consequently, this increased holding force could ultimately damage, perforate or sever the tissue held between the jaws.

German Patent document DE-A 40 10 775 discloses a surgical forceps having a fixed jaw and a movable jaw, which are connected to a fixed grip and a pivotable grip, respectively. The pivotable grip consists of two parts in alignment with each other. The two parts are unreleasably connected to each other by a spiral spring element. Detent elements or pawls are provided on the two parts of the pivotable grip, which are releasably engaged with each other. The holding force applied by the pivotable grip cannot be limited to a predetermined value. Consequently, the surgical forceps can damage blood vessels, tissue, or organs if a user inadvertently applies an excessive force during a surgical operation or procedure.

SUMMARY OF THE INVENTION

An object of the present invention is to ensure that the holding force exerted by the jaws of a surgical instrument is regulated such that damage to a patient's tissue being gripped by the instrument can be avoided.

Another object of the present invention is to provide a surgical instrument which will grip tissue up to a maximum predetermined value which remains constant, even when a user applies an increasing amount of pressure through the handle.

Still another object is to provide a surgical instrument or forceps which is substantially immune from becoming overstressed so that the possibility is minimized of breaking the surgical instrument and scattering pans thereof into a body cavity of a patient.

The surgical instrument of the present invention includes a handle at its proximal end, a pair of gripping jaws at its distal end, and a force transfer and limiting member operatively connecting the handle to the gripping jaws for transmitting and limiting user-applied force therebetween. The squeezing of the handle grips relative to each other is limited by a stop to ensure that a user does not permanently deform the material forming the force transfer and limiting member. The force transfer and limiting member is preferably made of a material that is superelastic, i.e. reversibly deformable such that it returns to its original physical shape or form after the material has been deformed.

The deformation characteristics of this superelastic material are such that upon the application of a compressive (or stretching) force the material compresses until a certain point and remains or plateaus at this point as the force increases until a threshold value is reached. The material comprising the force transfer and limiting member may, for example, be an alloy which is superelastic or pseudoelastic. An example of such material are known Ni-Ti based alloy, that had been properly heat treated. The material at its superelasticity range behaves analogously to a rubber band such that it can sustain relatively large or substantial deformation within a given range or stress without substantial increase in the applied force. Thus, when the material is stressed within this superelastic range, even after it has expanded or extended up to 8% of the original dimension, the material returns to its original shape after the applied force is removed. By using such a superelastic material in forming the force transfer and limiting member, the closure force applied by the jaws of the forceps of the present invention is limited to a predetermined maximum closure force, even when the handle is squeezed further. The force transfer and limiting member, however, is suitably sized and shaped and the relative travel of the handle grips is appropriately limited so that deformation of the force transfer and limiting member remains within the superelastic range and below the breaking or rupture point of the material.

In a first embodiment of the present invention, the pair of pivotable jaws of the forceps are operatively connected through a force transfer element to a pair of handle grips so that movement of the grips causes corresponding movement of the jaws. By bringing the grips together, the jaws close. The force transfer and limiting member is a tubular push-pull rod slidably mounted within a tubular shaft. The tubular shaft is connected at its proximal end to the handle and at its distal end to the jaws. The handle comprises a fixed grip which is rigidly connected to the tubular shaft and a movable grip pivotably connected to the fixed grip. The push-pull rod is pivotably connected to at least one of the jaws at its distal end and pivotably connected to the movable handle grip at its proximal end. Thus, when the jaws are operatively engaged, the push-pull rod is subjected to tension. At the maximum allowable closure force, the stress in the push-pull rod reaches its superelasticity range so that further increase in applied force will merely stretch the rod without causing the closure force applied to the jaws to increase and/or exceed the predetermined maximum allowable value.

According to another embodiment of the present invention, the force transfer and limiting member is constructed as a tension or compression spring guided in the tubular shaft. The proximal end of the spring connected to the handle grip and the distal end of the tension spring is connected to at least one of the jaws.

In still another embodiment of the present invention, the forceps is a scissor-like surgical instrument wherein at least one of the gripping members has, as an integral component, an intermediate portion made of the form-memory alloy which serves as a force transmitting and limiting member.

Other objects and features of the present invention will become apparent from the following detailed description considered in conjunction with the accompanying drawings. It is to be understood, however, that the drawings are

3 intended solely for purposes of illustration and not as a definition of the limits of the invention, for which reference should be made to the appended claims.

DETAILED DESCRIPTION OF THE DRAWINGS

In the drawings, wherein like reference numerals denote similar elements throughout the several views:

FIG. 1 is a partial sectional side view of a forceps constructed in accordance with a first embodiment of the present invention in an unclamped state;

FIG. 2 is a partial sectional view of the forceps shown in FIG. 1 in a clamped state;

FIG. 3 is a partial sectional side view of a forceps constructed in accordance with a second embodiment of the invention in a clamped state;

FIG. 4 is a partial sectional view of the forceps shown in FIG. 3 in an unclamped state;

FIG. 5 is a partial sectional side view of a forceps constructed in accordance with a third embodiment of the invention in a clamped state;

FIG. 6 is a partial sectional side view of the forceps shown in FIG. 5 in an unclamped state;

FIG. 7 is a partial sectional side view of a forceps constructed in accordance with a fourth embodiment of the invention in a clamped state;

FIG. 8 is a partial sectional side view of the forceps shown in FIG. 7 in an unclamped state;

DETAILED DESCRIPTION OF THE PRESENTLY PREFERRED EMBODIMENTS

Figure 9:
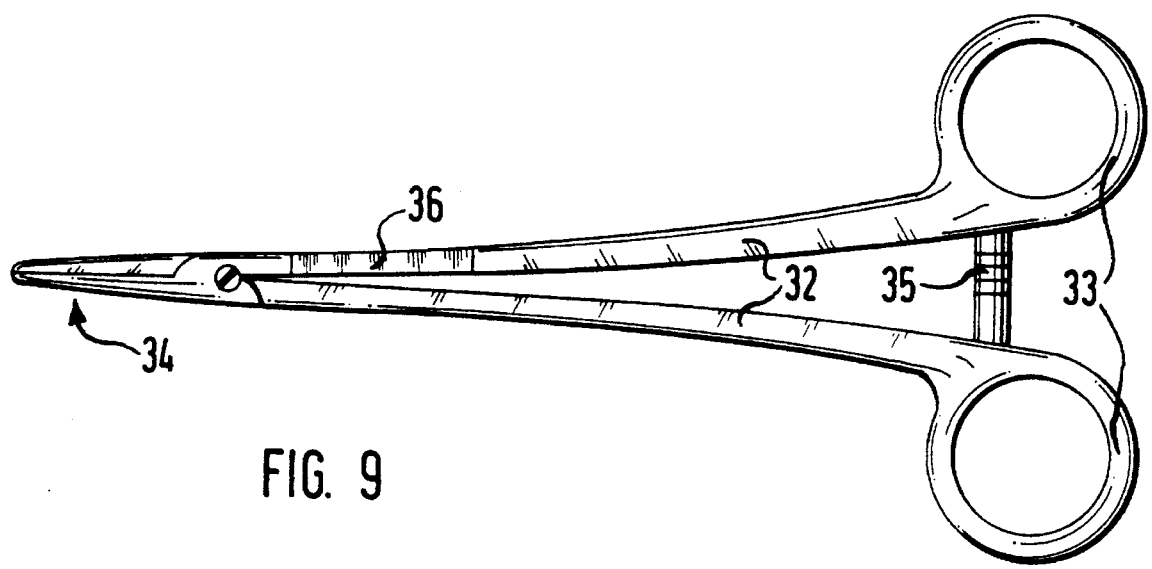
FIG. 9 is a side view of a forceps constructed in accordance with a fifth embodiment of the invention in a clamped state.

As shown in FIGS. 1 and 2, the forceps constructed in accordance with a first embodiment of the present invention comprises a tubular shaft 1, an effector which includes a pair of gripping jaws 2 pivotally mounted on the distal end of the shaft 1, and a handle 3 disposed at the proximal end of the shaft 1. It is contemplated within the scope of the present invention that the jaws 2 may also be constructed as scissor blades, or other types of gripping surfaces.

The handle 3 comprises a first grip or fixed arm 4 rigidly connected to the proximal end of the tubular shaft 1 and a second grip or movable arm 5 pivotably connected to the proximal end of the shaft 1 through a pin 6 mounted in a recess. A force transfer and limiting member constructed in the form of a pull-push rod 7 is slidably received or guided in the tubular shaft 1. The push-pull rod 7 is coupled at its proximal end to the movable arm 5, and at its distal end to the jaws 2 so that axial movement of the push-pull rod 7 is conveyed into swivelling action of the jaws 2 by well known means. Therefore, when movable arm 5 is pressed toward the fixed arm 4, the jaws 2 become operatively engaged and thereby move toward each other to a closed or gripping position.

Figure 10:
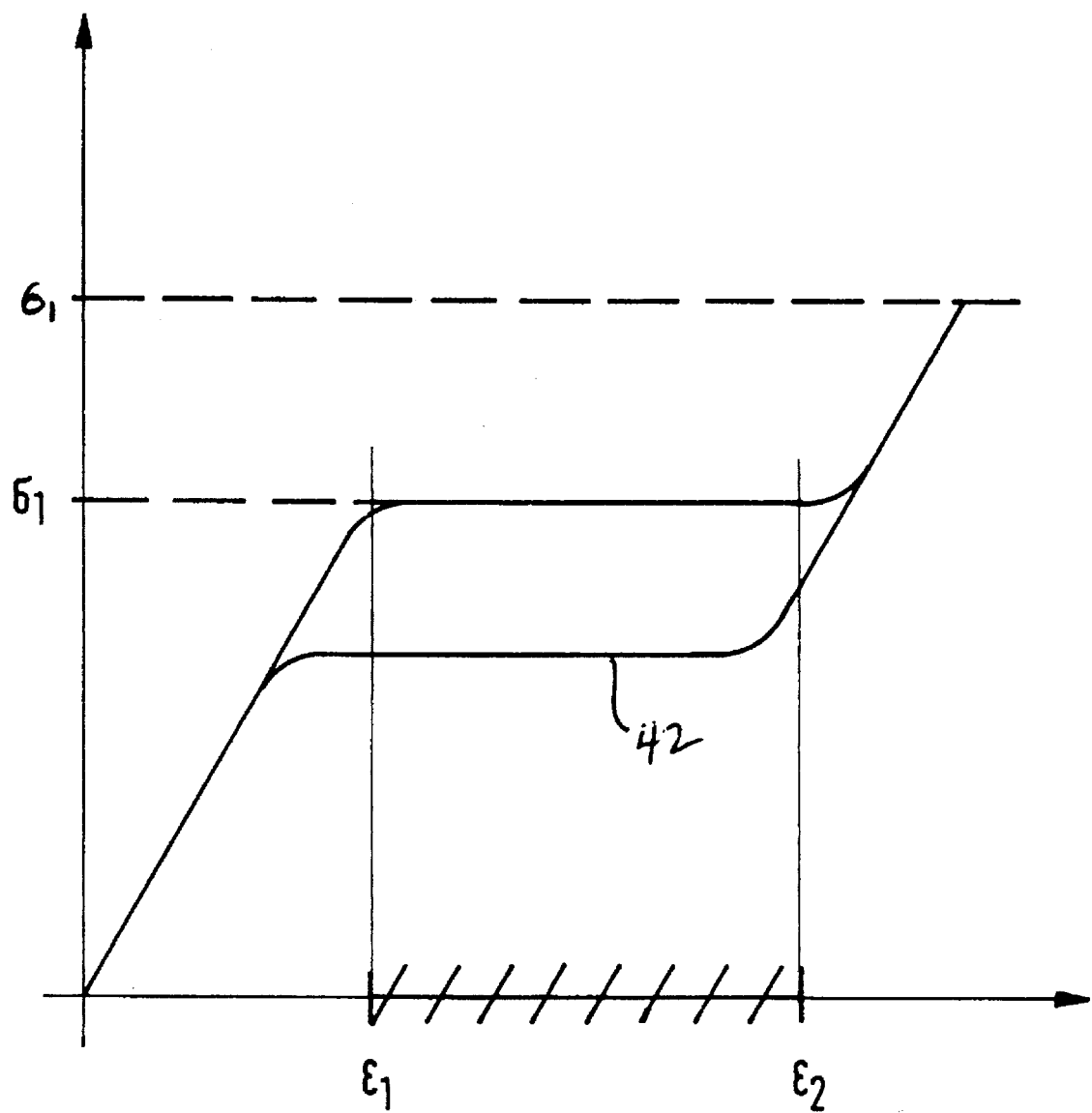
FIG. 10 is a representative stress-strain diagram of a superelastic material preferably comprising the force transfer and limiting rod of the forceps of the present invention.

The pull-push rod 7 is preferably made of a superelastic, reversibly deformable material having a memory of its physical form. The stress-strain characteristic of such a material is illustrated in FIG. 10. The material may, for example, be a suitably heat treated Ni-Ti alloy. When the jaws 2 reach their closed position, or when the jaws 2 meet resistance, for example by a piece of tissue interposed therebetween as shown in FIG. 2, the force exerted by the jaws increases with the actuating force applied to the arm 5. The force exerted by the jaws 2 increases until it reaches a value $\sigma_1$. If the arm 5 is moved further towards the arm 4, the pull-push rod 7 is extended during the expansion interval $\epsilon_1$–$\epsilon_2$ wherein the force exerted by jaws 2 remains substantially constant. The stress-strain characteristic of the material of the pull-push rod 7 thus runs through, or describes a stress plateau wherein the effective stress in the push-pull rod 7 is limited to the value $\sigma_1$ during the elastic expansion interval $\Gamma_1$–$\Gamma_2$. In order to prevent the expansion threshold value $\epsilon_2$ or correspondingly $\sigma_1$ from being exceeded, a stop 8 is preferably provided on or near the proximal end of the tubular shaft 1. The stop 8 abuts the arm 5 of the handle 3, to limit the pivotal movement of moveable arm 5 toward the fixed arm 4. FIG. 10 shows schematically that in the absence of stop 8, the closure force of the jaws 2 could rise beyond the aforementioned threshold $\sigma_1$ value to the extent that the push-pull rod 7 risks permanent plastic deformation and/or breakage of the push-pull rod 7 and the forceps. Therefore, the threshold value $\epsilon_2$ is preferably selected so that such damage cannot occur. When the force on the movable arm 5 is released, the push-pull rod 7, because of its preferred reversibly deformable composition, elastically contracts and reassumes its initial physical form as it follows the lower horizontal line 42 of the hysteresis loop depicted in FIG. 10. Thus, an instrument constructed in accordance with the present invention will not crush or damage an object such, for example, as tissue or cartilage, gripped between the jaws. Moreover, the instrument cannot be overstressed.

A second embodiment of the forceps of the present invention is shown in FIGS. 3 and 4 which also comprises a tubular shaft 11 which includes at its distal end a pair of pivotable jaws 12, and at its proximal end a handle 13. The handle 13 has a first grip or fixed arm 14 integrally formed with the proximal end of the shaft 11 and a second grip or movable arm 15 which is pivotably mounted, using pin 16, and is thus pivotable relative to the fixed arm 14. An actuating rod 17 slidably received or guided in the shaft 11, is coupled at its distal end to the jaws 12 and is connected at its proximal end to the movable arm 15. The movable arm 15 comprises a finger grip or an actuating part 18, an upper part 19 connected to the rod 17, and a force transfer and limiting member constructed as a bendable member or an intermediate rod 20 formed of the superelastic material, similar to that used for push-pull rod 7 of the first embodiment discussed above. As is apparent from FIGS. 3 and 4, the travel of the actuating part 18 toward the fixed arm 14 is limited by the fixed arm 14 which is appropriately shaped and dimensioned so as to act as a stop when the handle grips are squeezed together.

As depicted in FIG. 3, the intermediate rod 20 is controllably and elastically deformed when the closure force of the jaws 12 exceeds a desired pressure value. The desired value is selected so that the object being gripped between the jaws does not become damaged by the gripping force and so that the forceps cannot be overstressed. The intermediate rod 20 deforms in the manner described schematically by FIG. 10. The superelastic deformation starts at $\sigma_1$ and $\epsilon_1$ and continues to $\epsilon_2$. Preferably the arms 14 and 15 are appropriately sized and shaped so that confronting surfaces of respective arms 14 and 15 rest against each other when strain $\epsilon_2$ is reached.

In the third and fourth embodiments of the present invention shown in FIGS. 5 and 6, and 7 and 8 respectively, the forceps each comprise a tubular shaft 21, a pair of pivotally mounted jaws 22 at its distal end, and a handle 23 at its proximal end. The handle 23 comprises a first grip or fixed arm 24 and a second grip or movable arm 25. The movable arm 25 is pivotably mounted about a pin 26 and movable relative to the fixed arm 24. In these embodiments, the shaft 21 has an enlarged, tubular, proximal extension 27. The fixed arm 24 is shaped and sized so as to act as a stop for the movable arm 25 in a way similar to that of the second embodiment shown in FIGS. 3 and 4.

The forceps of the present invention depicted in FIGS. 5 and 6 comprises a force transfer and limiting member which is in the form of a tension spring 31 slidably received or guided within the extension 27 of the tubular shaft 21. The distal end of the spring 31 is connected to the pull-push rod 30. The pull-push rod 30 is connected to the jaws 22 at its distal end, and attached to the movable arm 25 at its proximal end. As depicted in FIG. 5, when a user squeezes the trigger grip causing the movable arm 25 to be pressed toward the fixed arm 24, the spring 31 is pulled or subjected to tensile stress and push-pull rod 30 is correspondingly pulled. The deformation characteristics of the spring 31 are preferably such that the closure force applied to the jaws 22 is limited so as to avoid damaging an object grasped by the forceps or the forceps itself. FIG. 6 depicts a portion of the forceps shown in FIG. 5 but in an unclamped state. In FIG. 6, spring 31 is not stretched by movable arm 25.

The embodiment of the present invention shown in FIGS. 7 and 8 comprises an extension 27, to which the arm 24 is fixed. The force transfer and limiting member is in the form of a compression spring 28 slidably received or guided within extension 27. The compression spring 28 is preferably made of an alloy having physical form memory properties or superelastic properties described above. Within the extension 27 is a tube 29 within which the compression spring 28 is accommodated. The tube 29 is movable longitudinally within the extension 27. The tube 29 has a substantially closed distal end which engages the distal end of the spring 28. The tube 29 is coupled at its proximal end to the movable arm 25. The proximal end of the compression spring 28 is connected to a pull-push rod 30 which slidably passes through a hole in the distal end of the tube 29. The push-pull rod 30 is coupled at its distal end to the jaws 22.

Referring to FIG. 7, when the movable arm 25 is pressed toward the fixed arm 24 by squeezing the finger grips, movable arm 25 pulls tube 29 which compresses compression spring 28. The deformation characteristics of the spring 28 are preferably such that the closure force applied to the jaws 22 does not damage the object held therebetween or the forceps itself. FIG. 8 depicts a portion of the forceps shown in FIG. 5 but in an unclamped state. In FIG. 8, spring 28 is not compressed by movable arm 25 and tube 29.

The scissor-like medical instrument or forceps of the fifth embodiment of the present invention shown in FIG. 9 is comprised of a pair of pivotally connected gripping members or arms 32. Each of the arms 32 has a proximal finger grip 33 and a distal jaw 34. A detent device or pawl 35 is provided between the finger grips 33 to act as a stop to limit the opening of the arms 32. A medical instrument such as, for example, a needle holder, must be able to apply a maximum constant gripping force without danger of being overstressed to ensure that the forceps do not break or fracture during a surgical operation, in which case broken parts may fall into an open wound or other body cavity. Accordingly, at least one of the arms 32 is provided with an intermediate force transfer and limiting portion 36 as an integral component of at least one of the arms. The portion 36 is preferably comprised of a superelastic alloy having physical form-memory properties as discussed above, so that the force exerted by the jaws 34 is always limited to a predetermined value without causing damage to the object being gripped or to the forceps itself.

Thus, while there have been shown and described and pointed out fundamental novel features of the invention as applied to preferred embodiments thereof, it will be understood that various omissions and substitutions and changes in the form and details of the devices illustrated, and in their operation, may be made by those skilled in the art without departing from the spirit of the invention. For example, it is expressly intended that all combinations of those elements which perform substantially the same function in substantially the same way to achieve the same results are within the scope of the invention. Substitutions of elements from one described embodiment to another are also fully intended and contemplated. It is also to be understood that the drawings are not necessarily drawn to scale but that they are merely conceptual in nature. It is the intention, therefore, to be limited only as indicated by the scope of the claims appended hereto.

What is claimed is:

1. A surgical instrument for handling an object, the instrument having a distal end and a proximal end, comprising:

a pair of jaws disposed at the distal end of the instrument for gripping the object;

an actuatable handle disposed at the proximal end of the instrument; and a reversibly deformable force transfer and limiting member for transferring to said jaws a force imparted to said member by actuation of said handle, said force transfer and limiting member having a distal end operatively connected to said pair of jaws for operatively effecting movement of said jaws relative to one another, and said member having a proximal end operatively connected to said handle for imparting the force from actuation of said handle to said force transfer and limiting member, said force transfer and limiting member comprising a pseudoelastic material through which the force is transferred from said handle to said jaws and selected so that the force transferred by said member to said jaws is no greater than a predetermined value defined by a stress plateau of said pseudoelastic material such that the object gripped between said jaws is not damaged by the force imparted to said member by actuation of said handle.

2. The instrument of claim 1, wherein said handle comprises a first and a second grip movable relative to each other.

3. The instrument of claim 1, wherein said force transfer and limiting member comprises:

a shaft having an axial bore extending therethrough; and a push-pull rod slidably disposed within the axial bore of said shaft, said push-pull rod having a distal end and a proximal end, the distal end of said push-pull rod being operatively connected to said jaws, the proximal end of said push-pull rod being operatively connected to said handle.

4. The instrument of claim 3, wherein said push-pull rod is comprised of a superelastic material.

5. The instrument of claim 1, further comprising a stop for limiting the actuation of said handle.

6. The instrument of claim 1, wherein said pseudoelastic material of said force transfer and limiting member further comprises a superelastic material.

7. The instrument of claim 3, further comprising an intermediate rod interposed between said push-pull rod and said handle.

8. The instrument of claim 3, wherein said intermediate rod is comprised of a superelastic material.

9. The instrument of claim 3, further comprising a spring assembly interposed between said push-pull rod and said handle.

10. The instrument of claim 9, wherein said spring assembly has an extended position corresponding to a closed position of said jaws.

11. The instrument of claim 9, wherein said spring assembly has a compressed position corresponding to a closed position of actuation of said handle.

* * * * *